United States Patent [19]
Rincoe et al.

[11] Patent Number: 5,246,465
[45] Date of Patent: Sep. 21, 1993

[54] PROSTHETIC KNEE JOINT

[75] Inventors: Richard G. Rincoe, 49 S. Holman Way, Golden, Colo. 80401; Marlin B. Hull, Golden, Colo.

[73] Assignee: Richard G. Rincoe, Golden, Colo.

[21] Appl. No.: 687,831

[22] Filed: Apr. 19, 1991

[51] Int. Cl.⁵ .................. A61F 2/62; A61F 2/10; A61F 2/64; B25J 11/00
[52] U.S. Cl. ........................ 623/39; 623/24; 623/25; 623/44; 901/21
[58] Field of Search .............. 623/25, 39, 43, 44, 623/45, 53, 55, 24, 64; 901/21, 25, 28

[56] References Cited

U.S. PATENT DOCUMENTS

| | | | |
|---|---|---|---|
| 2,282,952 | 5/1942 | Erickson | 623/43 X |
| 2,393,142 | 1/1946 | Caron | 623/43 X |
| 2,662,228 | 12/1953 | Bennington | 623/24 |
| 2,701,370 | 2/1955 | Alderson | 623/66 X |
| 3,553,738 | 1/1971 | Liberson | 623/24 |
| 3,790,002 | 2/1974 | Germand et al. | 901/21 X |
| 3,837,010 | 9/1974 | Prout | 623/43 X |
| 4,090,264 | 5/1978 | Thompson | 623/44 |
| 4,094,016 | 6/1978 | Eroyan | 623/24 |
| 4,135,254 | 1/1979 | Weber et al. | 623/43 |
| 4,232,405 | 11/1980 | Janovsky | 623/43 X |
| 4,259,876 | 4/1981 | Belyanin et al. | 901/21 X |
| 4,370,761 | 2/1983 | Serri | 623/43 |
| 4,387,472 | 6/1983 | Wilson | 623/24 X |
| 4,392,776 | 7/1983 | Shum | 901/21 X |
| 4,520,512 | 6/1985 | Lehneis et al. | 623/39 |
| 4,693,663 | 9/1987 | Brenholt et al. | 901/21 X |
| 4,708,578 | 11/1987 | Richter | 901/21 X |
| 4,865,376 | 9/1989 | Leaver et al. | 901/21 X |
| 4,955,250 | 9/1990 | Fisher | 901/28 X |
| 4,986,723 | 1/1991 | Maeda | 901/21 X |
| 5,013,326 | 5/1991 | Horvath | 623/64 |
| 5,020,388 | 6/1991 | Maeda | 901/21 X |
| 5,062,673 | 11/1991 | Mimura | 623/64 X |
| 5,080,682 | 1/1992 | Schectman | 623/24 X |
| 5,119,687 | 6/1992 | Naruoka et al. | 901/25 X |
| 5,129,279 | 7/1992 | Rennex | 901/28 X |

Primary Examiner—David Isabella
Assistant Examiner—Elizabeth M. Burke
Attorney, Agent, or Firm—Donald W. Margolis; Edwin H. Crabtree

[57] ABSTRACT

A robotic knee for mounting on an upper leg stump of an allows movement from a standing position to a normal walking position and then to a kneeling position and return to a standing position. A mounting plate receives the upper leg stump of an amputee. The knee includes a housing having a drive motor which can be rotated in one direction to bend the knee and then reversed to straighten the knee. The drive motor turns a worm gear which engages a main drive gear. A pair of extension pulleys is mounted on a main drive gear shaft attached to the main drive gear. A pair of extension cables is attached at a first end to the extension pulleys and wrapped thereon. A second end of the extension cables is attached to a front portion of a mounting plate. A pair of flexion pulleys is also attached to the main drive gear. A pair of flexion cables is attached at a first end to the flexion pulleys and wrapped thereon. A second end of the flexion cables is attached to a rear portion of the mounting plate. On a bottom of the mounting plate is disposed a rack with rack teeth. The rack teeth engage a walking gear segment, thereby allowing the mounting plate to be moved up and down in a rocking motion by the extension and flexion cables, the rack teeth rock on the walking gear segment allowing the knee to simulate a natural rocking motion.

20 Claims, 3 Drawing Sheets

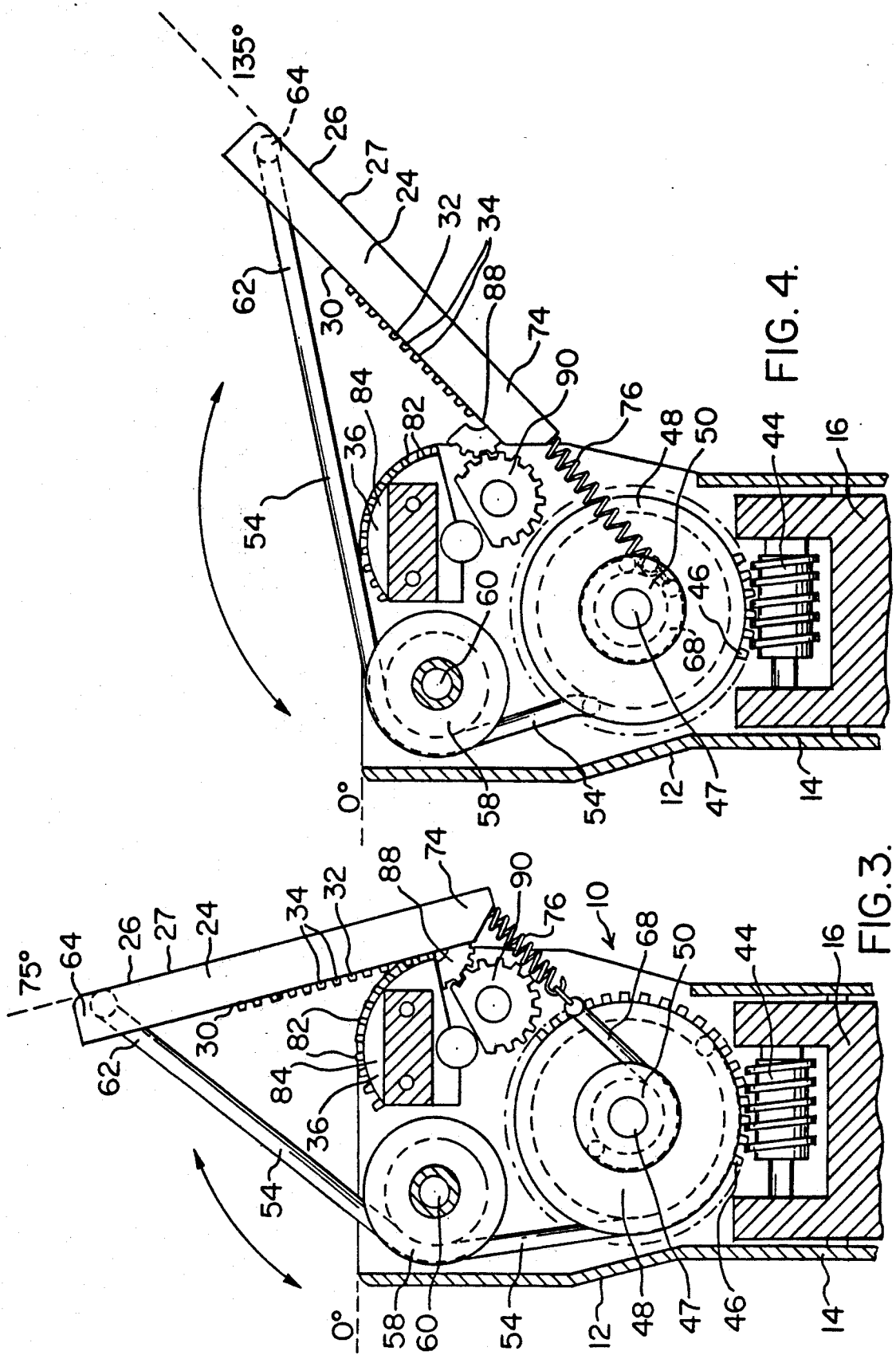

PROSTHETIC KNEE JOINT

BACKGROUND OF THE INVENTION (a) Field of the Invention

This invention relates to a prosthesis for a limb amputee who has lost his knee or a portion of the thigh and femur above the knee, and to such a prosthetic or robotic knee joint which can be myoelectrically controlled and which can be driven by a conventional power source.

(b) Discussion of the Prior Art

Heretofore there have been a variety of prostheses that are controlled myoelectrically using neural signals, and responding bioelectrically. These devices and systems for controlling artificial limbs are described in U.S. Pat. No. 3,735,425 to Hoshall et al; U.S. Pat. No. 4,878,913 to Aebischer et al; U.S. Pat. No. 3,501,776 to Beeker et al; U.S. Pat. No. 3,491,378 to Ioffe et al; and U.S. Pat. No. 4,792,338 to Rennerfelt. While the above mentioned patents discuss broadly methods and systems for operating a prosthesis, and more specifically for controlling an artificial arm or hand, none of the above-mentioned patents disclose an improved knee prosthesis which allows the user of the prosthesis to simulate natural positions and motions of a normal human knee.

In U.S. Pat. No. 3,453,663 to Minor and U.S. Pat. No. 3,800,334 to Friberg, two different types of artificial legs are shown for above-knee amputees. The artificial legs include a thigh section, a shank section, a foot section, an ankle joint, and a pivotal knee joint. Each of these artificial legs incorporates a single pivot to simulate the movement of the knee and therefore do not allow or provide for the complex movements of a normal knee into the artificial leg.

In U.S. Pat. No. 4,614,518 to Lehneis et al an artificial limb is disclosed having two limb members connected by a knee joint provided with rotator members. The rotator members are cylindrical with one forming a rotatable sleeve about the other. The rotator members rotate about a single pivot and this artificial limb does not allow or provide for the complex movements necessary to simulate the operation of a normal knee.

In U.S. Pat. No. 4,379,350 to Munny a prosthetic joint for knee and above-knee amputees is disclosed having an articulated joint with an arcuate rack, a rectilinear rack, and a pinion mounted on a slide and engaging the two racks. This structure of the articulated joint allows for a rotary and sliding movement of the knee. The type of knee movement provided by this prosthetic joint fails to simulate the natural rocking motion of the human knee.

None of the above-mentioned patents describe or disclose teachings similar to the subject robotic knee and its unique features and modes of operation as described herein.

SUMMARY OF THE INVENTION

The present invention, as disclosed herein, includes a knee housing having a drive motor mounted therein that rotates in one direction to bend the knee. When the rotation of the drive motor is reversed, the knee is straightened. The drive motor may be powered by a battery pack or any other suitable power source. A worm gear is mounted on the rotatable shaft of the drive motor. The worm gear engages a main drive gear. A pair of extension pulleys are mounted on a main drive gear shaft attached to the main drive gear. A pair of extension cables is attached at a first end to the extension pulleys and wrapped thereon. A second end of the extension cables is attached to a front end of a substantially flat mounting plate, and provides ample space for attachment to the upper leg stump of an amputee on the top thereof. A pair of flexion pulleys are also attached to the main drive gear. The first ends of a pair of flexion cables are attached to the flexion pulleys and wrapped therearound. The second ends of the flexion cables are attached to a rear end of the flat mounting plate. On the bottom of the mounting plate is a rack with rack teeth. The rack teeth engage a walking gear segment. As the mounting plate is moved up and down in a rocking motion by the extension cables and the flexion cables, the rack teeth rock on the walking gear segment allowing the robotic knee to simulate the natural rocking motion of the human knee.

When the knee is rotated past a 75° position, two smaller gear segments engage the rack teeth, and the knee can continue to roll on the gear segments to a 135° position for kneeling. This feature of the robotic knee prevents the upper leg stump from engaging a lower artificial leg when bending the knee past 90°.

The knee may be programmed for automatic walking and stair climbing in conjunction with an automatic ankle. The speed of the drive motor can be adjusted to provide for different walking and stair climbing speeds.

These and other objects of the present invention will become apparent to those skilled in the art from the following detailed description, showing the contemplated novel construction, combination, and elements as herein described, and more particularly defined by the appended claims, it being understood that changes in the precise embodiments of the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 3 is a side views of the robotic knee in a sitting;

FIG. 4 is a side view of the robotic knee in the position and walking and kneeling position;

DETAILED DESCRIPTION OF THE PREFERRED EMBODIMENT

Figure 1:
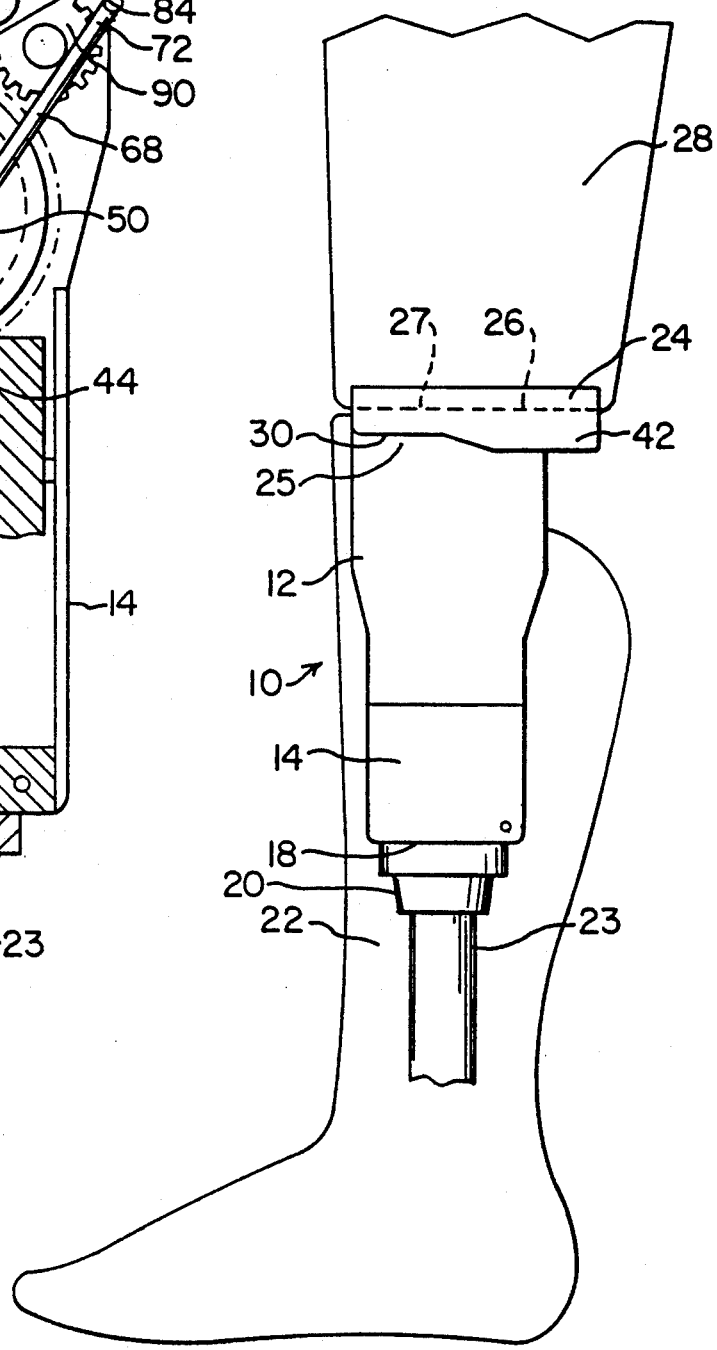
FIG. 1 is a left side view of the robotic knee with a flat mounting plate shown receiving an upper leg stump on top thereof and an artificial leg, ankle and foot below.

In FIG. 1 a side view of the robotic knee is shown having general reference numeral 10. The front of the knee 10 is to the left of the drawing and the rear of the knee 10 to the right of the drawing. The knee 10 includes a knee housing 12 with a lower portion 14 of the housing 12 receiving a drive motor 16 therein. The drive motor 16 is shown in FIG. 2 Attached to a bottom 18 of the housing 12 is a lower leg socket 20 for attachment to a connecting tube 23 which is part of an artificial lower leg 22.

Figure 5:
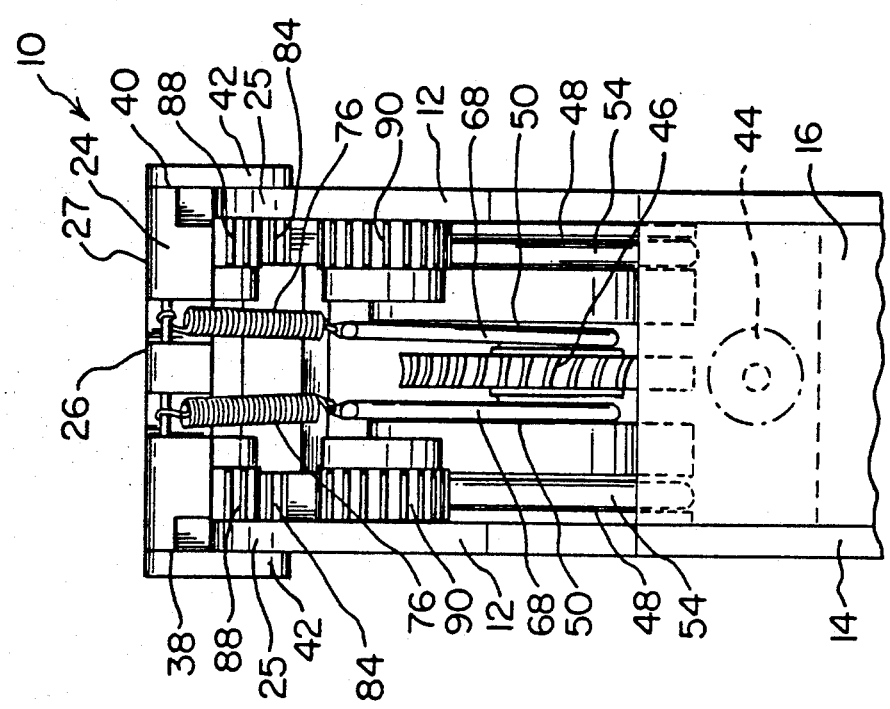
FIG. 5 is a rear view of the robotic knee shown in FIG. 2.

A mounting plate 24 is disposed on an upper portion 25 of the housing 12. The mounting plate 24 has a large flat surface 26 in a top 27 of the plate 24 for attaching various sizes of an upper leg stump 28. A bottom 30 of the mounting plate 24 includes a pair of elongated parallel gear racks 32 with gear teeth 34 for meshing with a pair of walking gear segments 36 which are attached to the sides of the housing 12. The gear racks 32, teeth 34, and gear segments 36 are shown in FIGS. 2, 3, 4, and 5. It should be noted that the distance from the top of the mounting plate 24 to a pivot point of the racks 32 on the gear segments 36 is approximately ½ inch, or less, thereby allowing a very low amputation point on the upper leg stump 28. Mounted on a side 38 and an opposite side 40 of the mounting plate 24 as shown in FIG. 5 is a pair of side support bars 42 which provide lateral support for the mounting plate 24 as it moves from a retracted position to an extended position and returns to the retracted position.

Figure 2:
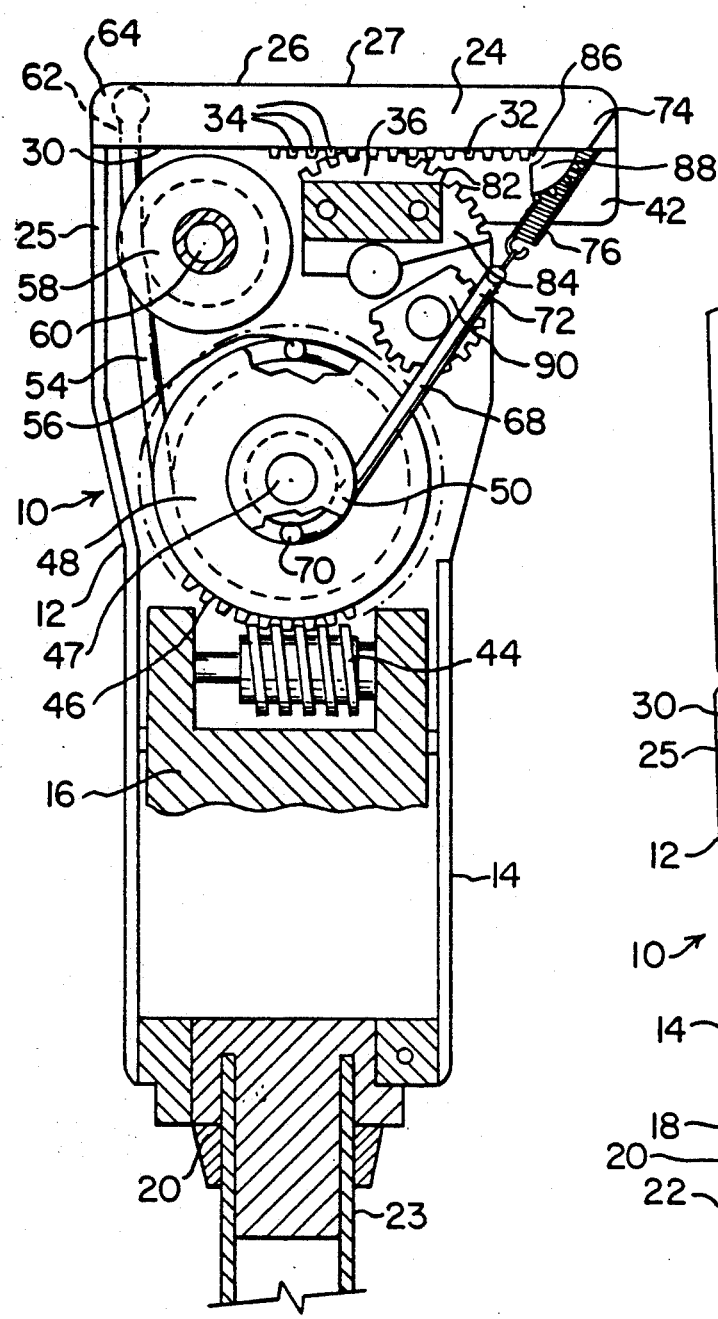
FIG. 2 is an enlarged cut away side view of the robotic knee of FIG. 1 showing a drive motor and the internal gearing of the knee.

In FIG. 2 a side view of the robotic knee 10 is shown with the housing 12 cut away to expose the inner workings and illustrate how the drive motor 16 is coupled with the mounting plate 24 to move the mounting plate 24 attached to the amputated lower leg stump 28 from a standing position, with the plate 24 horizontal, to a walking or sitting position at an angle in the range of 75° from the horizontal as shown in FIG. 3, and to a kneeling position at an angle in the range of 135° from the horizontal as shown in FIG. 4.

The drive motor 16 rotates a worm gear 44 which drives a main drive gear 46 having a drive shaft 47 rotatably mounted on the sides of the housing 12. Mounted on the drive shaft 46 and on opposite sides of the drive gear 46 is a pair of extension pulleys 48. Also on opposite sides of the main drive gear 46 and mounted on the drive shaft 46 is a pair of flexion pulleys 50.

A pair of stainless steel aircraft-type cables with a nylon coating are used as extension cables 54 having a first end 56 attached to the extension pulleys 48 and wrapped therearound. A portion of one of the pulleys 48 is shown in FIG. 2 cut away to show the first end 56 of the cable 54. The remainder of the cables 54 not wrapped around pulleys 48 is wrapped around a portion of a pair of front idle pulleys 58 having an idle pulley shaft 60 rotatably attached to the housing 12. The idle pulleys 58 are disposed in the upper front corner of the housing 12 and below the front of the mounting plate 24. A second end 62 of the extension cables 54 is attached to a front portion 64 of the mounting plate 24.

A second pair of stainless steel aircraft type cables with nylon coating is used as flexion cables 68 having a first end 70 attached to the flexion pulleys 50 and wrapped therearound. A portion of one of the flexion pulleys 50 is shown in FIG. 2 cut away to show the first end 70 of the cable 68. A second end 72 of the cables 68 is attached to a coil spring 76 which is attached to a rear portion 74 of the mounting plate 24.

Mounted on the bottom 30 of the mounting plate 24 are the elongated racks 32 with gear teeth 34. The gear teeth 34 mesh with gear teeth 82 of a walking gear segment 84. The gear segment 84 is secured to the housing 12. At the rear portion 74 of the mounting plate 26 and at one end 86 of the rack 30 is a quarter gear segment 88. This gear segment 88 engages a kneeling gear segment 90 when the mounting plate 24 moves from a sitting or walking position shown in FIG. 3 to a kneeling position shown in FIG. 4.

In FIG. 3 the mounting plate 24 has been moved upward from a horizontal or retracted position shown in FIGS. 1 and 2 to a walking or sitting position in a range of 75°. This is accomplished by the drive motor 16 and worm gear 44 rotating the drive gear 46 clockwise. When this occurs the flexion pulleys 50 begin to wrap the flexion cables 68 thereon. At the same time gear teeth 34 mesh with gear teeth 82 of the walking gear segment 84 and rotate the rack 32 and mounting plate 24 clockwise and to the rear of the knee housing 12. Also at the same time as the rear portion 74 of the mounting plate 24 moves rearward and downward, the extension cables 54 unwind from the extension pulleys 48 allowing the front portion 64 of the mounting plate 24 to move upward and rearward into the walking or sitting position. When the drive motor 16 and worm gear 44 rotate the drive gear 46 counter clockwise, the extension pulleys 48 retract the mounting plate 24 by winding the extension cables 54 thereon and at the same time the flexion cables 68 are unwound on the flexion pulleys 50 allowing the mounting plate 24 to return to its retracted and horizontal position. The springs 76 provide continuous tension on the flexion cables 68 as the cables 68 are wrapped and unwrapped on the flexion pulley 50.

In FIG. 4 the mounting plate 24 has been moved from a walking or sitting position to a kneeling position in range of 135°. When the drive gear 46 is driven clockwise and when the gear teeth 34 are rotated past the end of the walking gear segment 84, the quarter gear segment 88 engages the kneeling gear segment 90 allowing the mounting plate 24 to continue to rotate rearward and downward into a kneeling position in the range of 135° from the horizontal. When the direction of the drive motor 16 is reversed and the pulleys 48 and 50 rotated in a counter clockwise direction, the mounting plate 24 is rotated upward and forward back to a sitting position and then to a retracted or standing position. The mounting plate 24 with the gear teeth 34 meshing with the walking gear segment 84 and the quarter gear segment 88 meshing with the kneeling gear segment 90 maintain a smooth gear rotation movement while the knee 10 simulates the natural rocking motion of a human knee. The continuous meshing of the gear teeth prevent slipping during the operation of the robotic knee 10. Also the use of the quarter gear segment 88 meshing with the kneeling gear segment 90 prevents the upper leg stump 28 from engaging the lower artificial leg 22 when bending the robotic knee 10 past 90° as shown in FIG. 4.

In FIG. 5 a rear view of the robotic knee is illustrated. In this view both of the extension pulleys 48 and flexion pulleys 50 can be seen mounted on opposite sides of the main drive gear 46. Also the extension cables 54 and flexion cables 68 are seen wrapped around their respective pulleys 48 and 50. It should be added that through the use of a pair of extension cables 54 and flexion cables 68, should one of the cables break, the remaining cable can continue to operate the robotic knee 10 until the broken cable is repaired. Further seen in this view are the side support bars 42 mounted on opposite sides 38 and 40 of the mounting plate 24 and adjacent both sides of the top portion 25 of the housing 12. The support bars 42 insure against lateral movement of the mounting plate 24 on the gear segments 84 and 90 and any twisting that may occur due to rotation of the upper leg stump 28 on the mounting plate 24. Also, should the lower artificial leg 22 or knee housing 12 be twisted the support bars 42 would prevent lateral movement of the meshing gears described above.

Figure 6:
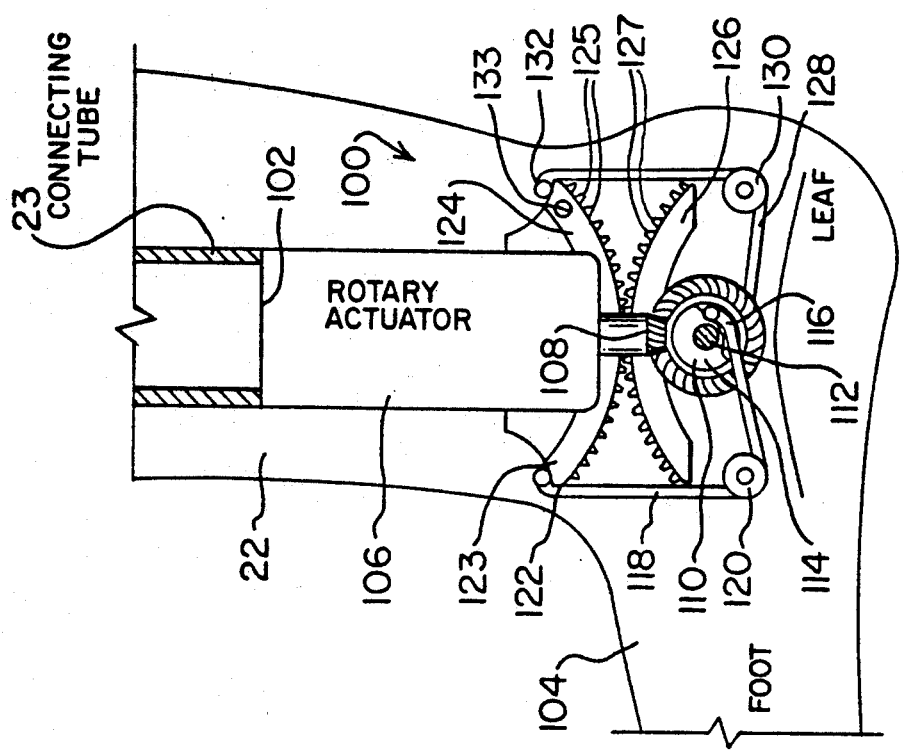
FIG. 6 is a robotic ankle which can be used with a lower artificial leg connected to the robotic knee.

In FIG. 6 a robotic ankle is illustrated and designated by general reference numeral 100. The ankle 100 is attached to a bottom 102 of the connecting 23 tube shown in FIGS. 1 and 2 and is driven in conjunction with the movement of the robotic knee 10 as described in FIGS. 3 and 4. The ankle 100 is also shown mounted in the rear top of an artificial foot 104.

The ankle 100 includes a drive motor 106 with pinion gear 108. The drive motor 106 can be provided electrical power from a battery pack or similar power source. The ankle 100, like the robotic knee 10, can be controlled by a myoelectric source or programmed and operated using microprocessors and the like.

The pinion gear 108 engages a main drive gear 110 having a main drive shaft 112 rotatably mounted on the artificial foot 104. The drive shaft 112 has an extension pulley 114 mounted thereon. A flexion pulley is disposed behind the main drive gear 110 and is not shown in the drawing. A first end 116 of an extension cable 118 is attached to the extension pulley 114 and wound thereon. The remainder of the extension cable 118 is wound on a portion of an extension idle pulley 120 with a second end 122 attached to a front end 123 of an ankle pivot gear segment 124. Gear teeth 125 of the gear segment 124 mesh with gear teeth 127 of a stationary gear segment 126.

A flexion cable 128 is attached at one end to the flexion pulley, not shown in the drawing, and wrapped thereon. The remaining portion of the flexion cable 128 is wrapped on a portion of a flexion idle pulley 130 with a second end 132 attached to a rear end 133 of the gear segment 124.

When the pinion gear 108 rotates the drive gear 110 in a clockwise direction, the flexion pulley wraps the flexion cable 128 thereon and the extension cable 118 is unwrapped from the extension pulley 114. This movement allows the pivot gear segment 124 to rock backward on the stationary gear segment 126 and the front of the artificial foot 104 to move downward in a natural rocking motion. When the pinion gear 108 rotates the drive gear 110 in a counter clockwise direction, the flexion pulley unwraps the flexion cable 128 and the extension cable 118 is wrapped on the extension pulley 114. This movement allows the pivot gear segment 124 to rock forward on the stationary gear segment 126 and the artificial foot 104 moves upward in a natural rocking motion.

It is therefore seen that the present invention provides a robotic knee for knee and above-knee amputees, which robotic knee can closely simulate the natural rocking motion of a human knee when an amputee is engaged in walking and stair climbing. It has been shown how the pivot point of the robotic knee can be located a very short distance from the upper leg stump mounting surface of an amputee, thus allowing, when there is a choice, a very low amputation point on the femoral stump. It has been shown how a large upper mounting plate on a robotic knee provides ample space for attachment of the robotic knee to the upper leg stump of an amputee. It has been taught how the use of wide rolling gear surfaces results in very low stress points in the robotic knee of the present invention, and how the use of meshed gear teeth in the robotic knee prevents slipping of the components making up the knee. The system by which the robotic knee of the present invention can be myoelectrically controlled, and easily driven by a drive motor, which when rotated in one direction bends the knee, and which when rotated in an opposite direction, straightens a bent knee has been shown.

While the invention has been particularly shown, described and illustrated in detail with reframe to preferred embodiments and modifications thereof, it should be understood by those skilled in the art that the foregoing and other modifications are exemplary only, and that equivalent changes in form and detail may be made therein without departing from the true spirit and scope of the invention as claimed.

The embodiments of the invention for which an exclusive privilege and property right is claimed are defined as follows:

1. A prosthetic knee for mounting on an upper leg stump, the knee comprising:
   a knee housing;
   a drive motor mounted in said knee housing for pivoting the knee;
   a mounting plate disposed on top of said knee housing for securing said knee to the upper leg stump, said mounting plate having a front portion, a rear portion, a top and a bottom, said mounting plate having at least one gear rack attached to said bottom thereof; and
   a gear assembly mounted in said knee housing and including:
   a main drive gear with drive shaft connected to said knee housing, said drive motor engaging said main drive gear;
   at least one extension pulley mounted on said drive shaft with one end of an extension cable attached to said extension pulley and a second end of said extension cable attached to said front portion of said mounting plate;
   at least one flexion pulley mounted on said drive shaft with one end of a flexion cable mounted on said flexion pulley and a second end of said flexion cable attached to a coil spring connected to said rear portion of said mounting plate; and
   at least one walking gear segment attached to said knee housing, said gear rack engaging said walking gear segment for pivoting said mounting plate from a first position to a second position.

2. The knee as described in claim 1 wherein said gear assembly includes at least one kneeling gear segment attached to said knee housing, said kneeling gear segment engaging a quarter gear segment mounted on one end of said gear rack when said mounting plate is pivoted from said second position to a third position.

3. The knee as described in claim 1 wherein said mounting plate includes a pair of side support bars attached to opposite sides of said mounting plate and disposed adjacent sides of the top of said knee housing.

4. The knee as described in claim 1 further including an artificial lower leg attached to a bottom of said knee housing.

5. The knee as described in claim 1 further including an artificial lower leg with a prosthetic ankle attached to a bottom of said knee housing.

6. The knee as described in claim 5 wherein said prosthetic ankle is attached to an artificial foot, said prosthetic ankle having means for raising and lowering said artificial foot.

7. A prosthetic knee joint system for mounting on a fermoral leg stump of an amputee, and which undergoes powered movement which simulates a standing position, a powered natural rocking or walking motion, a powered stair climbing motion, a sitting or kneeling position, or combination s thereof, with ease of movement from position to position, the prosthetic knee joint system including:

a housing, said housing having a top portion;

a drive motor attached to said housing;

attachment means located at the top portion of the housing, said attachment means having a top surface, a bottom surface, a front portion, and a rear portion, said top surface of said attachment means being designed to receive the femoral leg stump of an amputee, said rear portion of said attachment means designed to pivot away from said top portion of said housing;

a rotatably mounted shaft within said housing;

means for translating motion of said motor into rotation of said rotatably mounted shaft;

at least one first flexible line having a first end and a second end;

at least one first means for winding said at least one first flexible line, said at least one first means for winding connected to said rotatably mounted shaft for rotation when said shaft is rotated, said first end of said at least one first flexible line being associated with said at least one first means for winding, said at least one first flexible line being designed and positioned to be wrapped onto or played off of said at least one first means for winding with which it is associated in response to the rotation of said rotatably mounted shaft, and with said second end of said at least one first flexible line connected to said front portion of said attachment means;

at least one second flexible line having a first end and a second end;

at least one second means for winding said at least one second flexible line, said at least one second means for winding connected to said rotatably mounted shaft for rotation when said shaft is rotated, said first end of said at least one second flexible line being associated with said at least one second means for winding, said at least one second flexible line being designed and positioned to be wrapped onto or played off of said at least one second means for winding with which it is associated in response to the rotation of said rotatably mounted shaft, and with said second end of said at least one second flexible line connected to said rear portion of said attachment means;

at least one curved gear with gear teeth fixedly connected to the housing, said at least one curved gear normally positioned adjacent to and below said bottom surface of said attachment means;

at least one gear rack with gear rack teeth disposed on said bottom surface of said attachment means, said at least one gear rack normally being aligned with and in contact with said at least one curved gear, with at least some of said gear rack teeth of said at least one gear rack normally engaging some of said gear teeth of said at least one curved gear with which it is aligned and in contact; whereby, when said motor is activated it causes said means for translating the motion of said motor to cause rotation of said rotatably mounted shaft, which in turn causes said at least one first means for winding and said at least one second means for winding to rotate, resulting in said at least one first flexible line being either wrapped onto or played off of said at least one first means for winding with which it is associated, while at the same time said at least one second flexible line undergoes a reverse operation, and is either played off of or wrapped onto said at least one second means for winding with which it is associated, resulting in one of said at least one first and second flexible lines which is being wrapped onto a respective one of said at least one first and second means for winding with which it is associated pulling down a portion of said attachment means to which that line is connected, and another of said at least one first and second flexible lines which is played off of a respective one of said at least one first and second means for winding with which it is associated allowing a portion of said attachment means to which that line is connected to be raised in a manner such that said front portion or said rear portion of said attachment means may be caused to move up or down in a continuously pivoting or in a rocking motion by movement of said at leas tone first and second lines, with at least some of said gear rack teeth normally engaging and pivoting on some of said gear teeth, so that, depending upon direction and duration of activation of the motor, movement of the prosthetic knee joint system simulates a standing position, a powered natural rocking or walking motion, a powered stair climbing motion, a sitting or kneeling position, or combinations thereof, with each of powered movement from position to position.

8. The prosthetic knee joint system of claim 7 in which a worm gear is caused to rotate by said motor, and said worm gear in turn causes a drive gear, which carries said rotatably mounted shaft, to rotate.

9. The prosthetic knee joint system of claim 8 in which rotatably mounted shaft is a gear shaft.

10. The knee as described in claim 7 wherein said drive motor is an electric motor, and wherein said electric motor is controlled by myoelectric means.

11. The prosthetic knee joint system of claim 7 in which at least one of said at least one first means for winding and said at least one second means for winding are curved winding elements.

12. The prosthetic knee joint system of claim 11 in which at least one of said at least one first means for winding and said at least one second means for winding are pulleys.

13. The prosthetic knee joint system of claim 7 in which at least one of said at least one first and said at least one second flexible lines are cables.

14. The prosthetic knee joint system of claim 7 in which a resilient element is connected intermediate said second end of said at least one first flexible line and said front portion of said attachment means.

15. The prosthetic knee joint system of claim 14 in which said resilient element is a coiled spring.

16. The prosthetic knee joint system of claim 7 in which a pair of first winding means, a pair of first flexible lines, a pair of second winding means, and a pair of second flexible lines, are present and used in the system.

17. The prosthetic knee joint system of claim 7 in which a pair of curved gears are fixedly connected to the housing adjacent to and below said bottom surface of said attachment means, and a pair of gear racks are disposed on said bottom surface of said attachment means, with each gear rack being aligned with and in contact with one of said curved gears, with at least some of said gear rack teeth of each gear rack normally engaging some of said gear teeth of said curved gear with which it is aligned and in contact.

18. The prosthetic knee joint system of claim 7 in which a kneeling gear having gear teeth is fixedly located adjacent to and aligned with said at least one curved gear and below said bottom surface of said attachment means, and a quarter gear segment having gear teeth is mounted on said bottom surface of said attachment means adjacent to and aligned with said at least one gear rack and normally below said quarter gear segment; whereby when said at least one curved gear and an associated gear rack pivot said attachment means to a given position above horizontal, at least some of said gear teeth of said quarter gear segment are placed into contact with some of said gear teeth of said kneeling gear, and said teeth of said at least one gear rack are disengaged from said teeth of said at least one curved gear, thereby allowing additional rotation of said attachment means above the horizontal.

19. The prosthetic knee joint system of claim 18 in which said gear teeth of said quarter gear begin to engage said gear teeth of said kneeling gear when said attachment means reaches about 75° from the horizontal, and which is capable of extending to a position of a least about 135° from the horizontal.

20. A prosthetic knee joint system for mounting on a femoral leg stump of an amputee, and which undergoes powered movement which simulates a standing position, a powered natural rocking or walking motion, a powered stair climbing motion, a sitting or kneeling position, or combinations thereof, with ease of movement from position to position, the prosthetic knee joint system including:

a housing, said housing having a top portion;

an electric drive motor controlled by myoelectric means attached to said housing;

attachment means located at the top portion of the housing, said attachment means having a top surface, a bottom surface, a front portion, and a rear portion, said top surface of said attachment means being designed to receive the femoral leg stump of an amputee, said rear portion of said attachment means designed to pivot away from said top portion of said housing;

a worm gear within said housing, said worm gear positioned to be rotated by said motor;

a drive gear within said housing, said drive gear positioned to be rotated by said worm gear;

a rotatably mounted drive shaft carried by said drive gear within said housing, said drive shaft designed to be rotated when said drive gear rotates;

a pair of first flexible lines, each first flexible line having a first end and a second end;

a pair of first curved winding elements, each said first curved winding element connected to said drive shaft for rotation when said drive shaft is rotated by said drive gear, said first end of each said first flexible line being associated with one said first curved winding element, each first flexible line being designed and positioned to be wrapped onto or played off of said first curved winding element with which it is associated in response to rotation of said rotatably mounted shaft, and with said second end of each said first flexible line connected to said front portion of said attachment means;

a pair of second flexible lines, each having a first end and a second end;

a pair of second curved winding elements, each said second curved winding element connected to said drive shaft for rotation when said drive shaft is rotated by said drive gear, said first end of each said second flexible line being associated with one said second curved winding element, each second flexible line being designed and positioned to be wrapped onto or played off of said second curved winding element with which it is associated in response to the rotation of said rotatably mounted shaft, and with said second end of each said second flexible line connected to said front portion of said attachment means;

a pair of curved gears with gear teeth, each curved gear fixedly connected to the housing, each said curved gear normally positioned adjacent to and below said bottom surface of said attachment means;

a pair of gear racks with gear rack teeth, each gear rack disposed on said bottom of said attachment means, each gear rack normally being aligned with and in contact with one said curved gear, with at least some of said gear rack teeth of each gear rack normally engaging some of said gear teeth of said curved gear with which it is aligned and in contact; whereby, when said motor is activated it causes translation of motion of said motor to cause rotation of said rotatably mounted shaft, which in turn causes each first curved winding element and each second curved winding element to rotate resulting in each first flexible line being either wrapped onto or played off of each first curved winding element with which it is associated, while at same time each second flexible line undergoes a reverse operation, and is either played off of or wrapped onto each second curved winding element with which it is associated, resulting in each first or second flexible line which is being wrapped onto each first or second curved winding element with which it is associated pulling down a portion of said attachment means to which that line is connected, and each first or second flexible line which is played off of each first or second curved winding element with which it is associated allowing a portion of said attachment means to which that line is connected to be raised in a manner such that said front portion or said rear portion of said attachment means may be caused to move up or down in a continuously pivoting or in a rocking motion by movement of said first and second lines, with at least some of said gear rack teeth normally engaging and pivoting on some of said gear teeth, so that, depending upon direction and duration of activation of the motor, movement of the prosthetic knee joint system simulates a standing position, a powered natural rocking or walking motion, a powered stair climbing motion, a sitting or kneeling position, or combinations thereof, with each of powered movement from position to position.

* * * * *